United States Patent
Tremolada et al.

(10) Patent No.: US 10,280,394 B2
(45) Date of Patent: May 7, 2019

(54) DEVICE AND METHOD FOR PREPARING ADIPOSE TISSUE FOR TRANSPLANTATION

(71) Applicant: LIPOGEMS INTERNATIONAL S.P.A., Milan (IT)

(72) Inventors: Carlo Ferdinando Maria Tremolada, Milan (IT); Antonio Bosetto, Mirandola (IT); Paolo Pirazzoli, San Prospero (IT)

(73) Assignee: LIPOGEMS INTERNATIONAL S.P.A., Milan (IT)

( * ) Notice: Subject to any disclaimer, the term of this patent is extended or adjusted under 35 U.S.C. 154(b) by 186 days.

(21) Appl. No.: 15/126,759

(22) PCT Filed: Mar. 18, 2015

(86) PCT No.: PCT/IB2015/051992
§ 371 (c)(1),
(2) Date: Sep. 16, 2016

(87) PCT Pub. No.: WO2015/140737
PCT Pub. Date: Sep. 24, 2015

(65) Prior Publication Data
US 2017/0121666 A1 May 4, 2017

(30) Foreign Application Priority Data
Mar. 19, 2014 (IT) .............................. GE2014A0027

(51) Int. Cl.
*G01N 1/00* (2006.01)
*C12M 1/00* (2006.01)
(Continued)

(52) U.S. Cl.
CPC .......... *C12M 47/04* (2013.01); *A61M 1/0094* (2014.02); *C12M 29/00* (2013.01); *C12M 45/02* (2013.01); *A61M 2202/08* (2013.01)

(58) Field of Classification Search
None
See application file for complete search history.

(56) References Cited

U.S. PATENT DOCUMENTS

| | | | | |
|---|---|---|---|---|
| 2013/0123747 A1* | 5/2013 | Tremolada | ............. | C12M 45/02 604/506 |
| 2015/0004702 A1* | 1/2015 | Raj | ........................ | C12M 45/02 435/378 |

FOREIGN PATENT DOCUMENTS

| | | |
|---|---|---|
| WO | 95/24969 A1 | 9/1995 |
| WO | 2011/145075 A2 | 11/2011 |
| WO | 2013/144883 A2 | 10/2013 |

* cited by examiner

*Primary Examiner* — Jyoti Nagpaul
(74) *Attorney, Agent, or Firm* — Jeffrey N. Townes; Cozen O'Connor

(57) ABSTRACT

A device for preparing adipose tissue for transplantation, from lobular fat extracted, for instance, by liposuction. The device comprises at least one washing and separating container (1) having a washing chamber (11) for washing the liposuctioned material, which washing and separating container (1) has at least one inlet (12) and at least one outlet (13) for the liposuctioned material to enter the washing chamber (11) through the inlet (12) and for at least part of said material, the fluid component, to exit said chamber 11 through the outlet 13. The washing and separating container (1) is coupled to stirring means via coupling means (2) for releasably coupling said washing and separating container (1) to said stirring means, drive means being provided for driving said stirring means. The stirring means comprising a stirring member (31) supported by a support structure (32), said washing and separating container (1) being releasably coupled to said stirring member (31) via said coupling means, and said stirring member (31) being driven by said drive means, emulsion generating means (14) being pro- (Continued)

vided in said washing chamber (11), for generating an emulsion of the fluid components by mechanical stirring.

20 Claims, 14 Drawing Sheets

(51) Int. Cl.
*C12M 1/33* (2006.01)
*A61M 1/00* (2006.01)

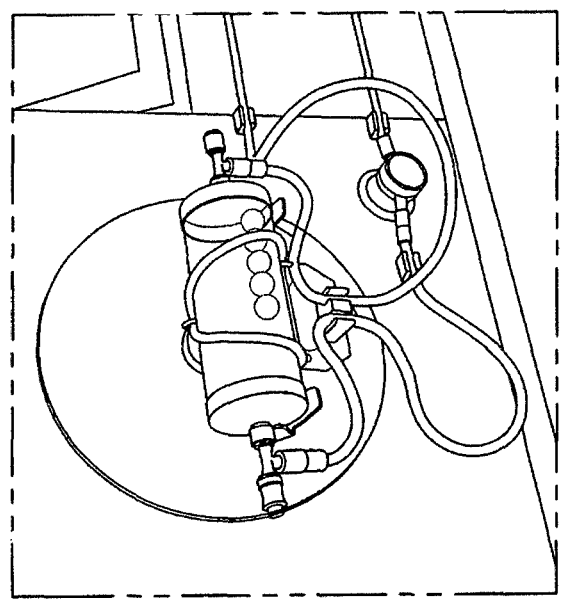
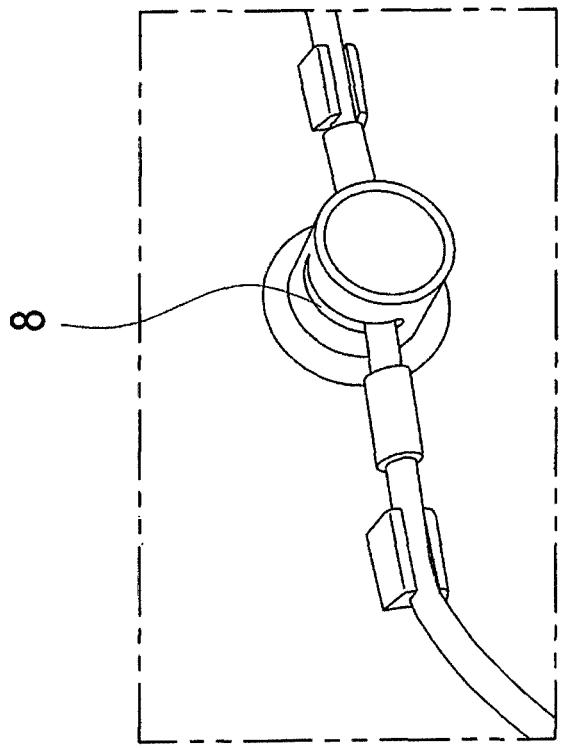
Fig. 2d
Fig. 2c

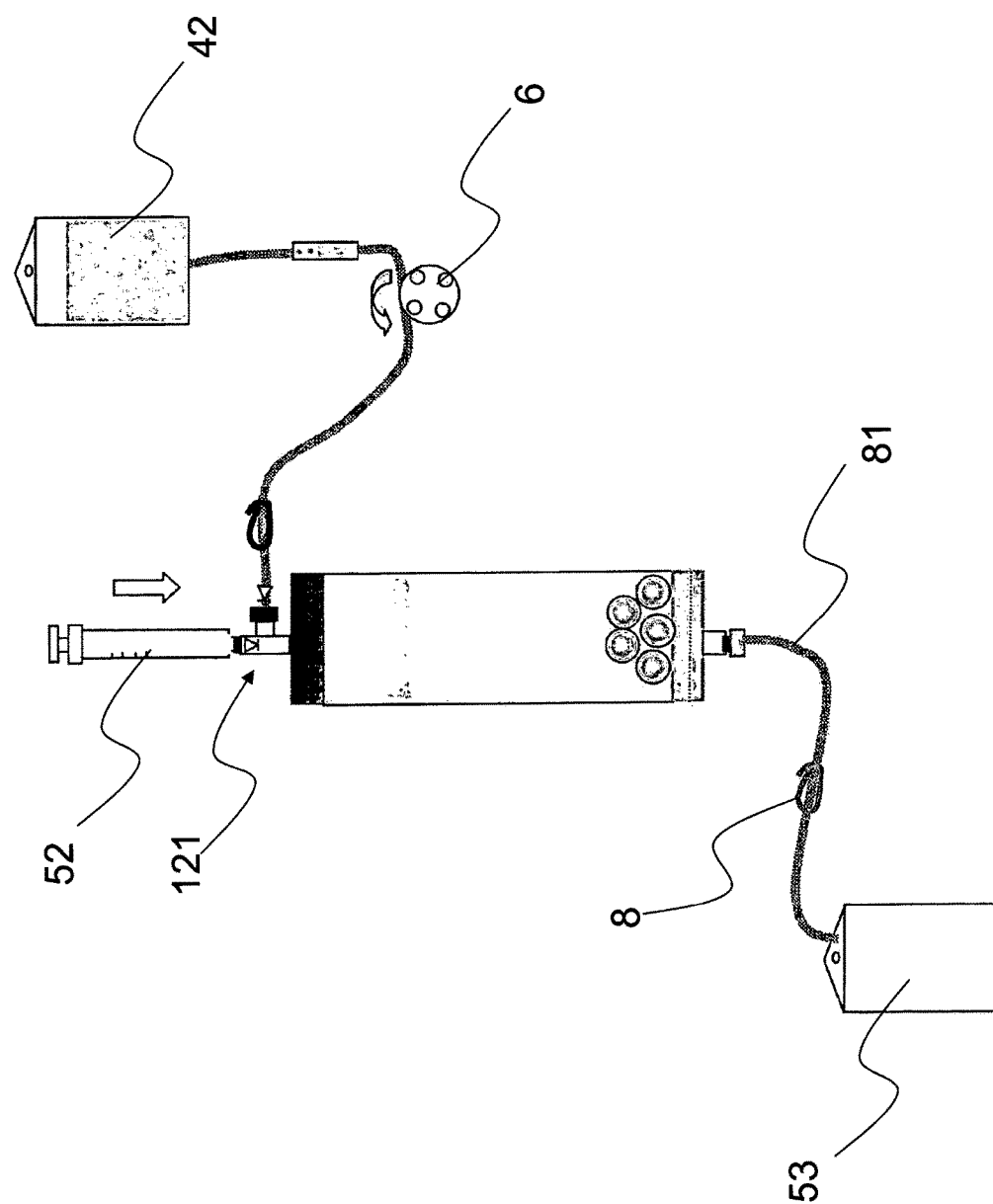

DEVICE AND METHOD FOR PREPARING ADIPOSE TISSUE FOR TRANSPLANTATION

CROSS-REFERENCE TO RELATED APPLICATIONS

This application is a national-stage application under 35 U.S.C. § 371 of PCT Application No. PCT/IB2015/051992, filed Mar. 18, 2015, which claims priority to Italian Patent Application No. GE2014A000027 filed Mar. 19, 2014, which are hereby incorporated by reference in their entirety.

The present invention relates to a device for preparing adipose tissue for transplantation, from lobular fat extracted, for instance, by liposuction.

The liposuctioned material generally consists of a solid component comprising cells (adipocytes) arranged in cell agglomerates (clusters) of heterogeneous sizes, a fluid component comprising an oily component derived from lysis of the adipocytes, blood residues and other liquid components, such as medicated saline solutions containing anesthetics, as used during the procedure.

The device of the present invention comprises at least one washing and separating container having a washing chamber for washing the liposuctioned material, which chamber has at least one inlet and at least one outlet, for the liposuctioned material to enter the washing chamber through the inlet and for at least part of said material, separated from the fluid component, to be removed from said chamber through the outlet.

According to the prior art, the preparation required for reuse of the liposuctioned material involves the separation of the cell component to be reinjected from the waste material composed of anesthetic liquid or biological fluids (serum or blood) and cell debris and oil resulting from the rupture of suctioned adipocytes.

Such separation may occur within the syringe that is used for withdrawal, or in special containers, essentially in three manners:

by sedimentation: the materials separate by differences in density under gravity, by centrifugation: the materials separate by differences in density under the effect of centrifugal force, by washing: the lipoaspirate is placed in a thin-mesh strainer and washed, generally with a saline, that may be progressively replaced or not.

According to the best known technique (Coleman lipostructure), the syringes containing the lipoaspirate are closed at the bottom by a luer-lock cap, and are placed in a centrifuge for separating the liquid phase from the solid biological material.

Before using the biological material so obtained, the anesthetic and biological liquids left on the bottom of the syringe after centrifugation shall be manually drained, by removing the luer-lock cap from the syringe and causing them to flow out by gravity, whereas the cell fragments and oil resulting from the break of the cell walls of adipocytes lie on the cell material to be transplanted and are removed in an incomplete and rudimentary manner, using sterile textile material upon which the centrifuged product is placed for the oil fraction to be absorbed and eliminated. This primitive procedure prevents collection and use of the entire liposuctioned material. Thus, the above described technique suffers from certain drawbacks.

First, the step of suction and separation by centrifugation causes a considerable amount of adipocytes to break and release much oil, which cannot completely removed with the Coleman technique, and makes a significant portion of the lipoaspirate unusable, i.e. the portion of cell material that, after centrifugation, is located on the upper part of the syringe barrel, in contact with oil, and hence is contaminated by said oil.

Due to the complexity of the above described procedure, the great number of required manual open surgery steps, the incomplete phase separation and the presence of oil in the biological filler to be injected increase the risk of infections and rejections, as well as the occurrence of possibly severe inflammation states.

Furthermore, the above described process involves multiple contacts of the liposuctioned material with surfaces of various types of instruments, as well as relatively long-time contact with air in a potentially non-sterile environment, whereby use thereof in a sterile field is prescribed. The long-time contact with air also causes oxidative stress in the cell material, and this may alter its characteristics and affect its function.

A technique is also known but rarely used, which involves mechanical fragmentation of the suctioned cell agglomerate using a blender, whose cutting blades separate fat lobules and provide an injectable cell suspension.

This fragmentation technique has many drawbacks.

First, the fragmentation step, which is followed by centrifugation, causes a considerable amount of adipocytes to break, preventing use of most of the liposuctioned material for later surgery. As a direct result, an increased number of liposuction sessions are required to compensate for this loss of material occurring during preparation of the material to be transplanted, with increased discomfort for patients.

Furthermore, the amount of usable cell suspension that can be obtained using the above described procedure and devices largely depends on the skill of the health care staff in setting the speed and operating time parameters of the blender and the centrifuge and on the conditions of the instruments: an excessive rotation speed of the blades or the use, for example, of a blender with poorly cutting blades does not cause separation of fat lobules, but rather the mechanical break of the cell walls of a large amount of adipocytes, which involves oil formation and makes the cell suspension unusable, in addition to requiring accurate separation of the cell fragments and oil from the suspension. This is because the presence of oil in the biological filler to be injected increases the risk of infections and rejections.

Furthermore, the above described process involves multiple contacts of the liposuctioned material with surfaces of various types of instruments, as well as some contact with air in a non perfectly sterile environment, as is the case of doctor's offices. Since the material is of biological nature, extended contact with air or with multiple instruments, that may even not be perfectly sterile, increases the risk of bacterial contamination, and may jeopardize treatment results.

The technique that involves washing through a strainer also has certain drawbacks.

Particularly the strainer net may easily become clogged with the liposuctioned material, which requires a manual action to remove fat from the meshes, thereby slowing down the preparation process and especially increasing the risk of contamination of the material to be injected.

The use of a simple strainer does not allow the liposuctioned material to be constantly maintained in a closed and perfectly sterile environment throughout the preparation process, i.e. from the liposuction step to the injection step.

A possible solution is disclosed in the International Patent Application WO2011/145075, by the Applicant hereof, the contents whereof are incorporated herein by reference.

Nevertheless, the solution provided by the above mentioned Patent Application, or at least some of the features of the device as claimed, may involve drawbacks in terms of the repeatability of the method.

This is because, as extensively described, stirring of the washing and separating container is a basic step in the preparation of the adipose tissue for transplantation, and it must be performed properly for transplantation to be successful.

Therefore, a stirring control is required to be implemented for the washing and separating container.

Thus, there is a yet unfulfilled need in the art for a device for preparing adipose tissue for transplantation that can obviate prior art drawbacks.

The present invention fulfills the above mentioned need by providing a device as described hereinbefore, in which the washing and separating container is coupled to stirring means via coupling means which releasably couple said washing and separating container to said stirring means.

Drive means are also provided for driving the stirring means.

The stirring means comprise a stirring member supported by a support structure: the washing and separating container is releasably coupled to the stirring member via the coupling means, and the stirring member is driven by the drive means.

Emulsion generating means are further provided in the washing chamber, for generating an emulsion of the fluid components by mechanical stirring.

This configuration provides automation of the washing and separation container stirring process, such that it can be repeatable, i.e. that it no longer relies on the manual skills of the surgeon.

The stirring process is standardized, thereby eliminating the variable component associated with human action.

This means that, once the movements of the washing and separation container have been decided, the same movements can be always accurately repeated to obtain the same product in the washing chamber, and particularly a product that has the desired properties for successful transplantation.

Preferably, the washing and separating container is a device as disclosed in the International Patent Application WO2011/145075.

Particularly, the washing and separating container consists of a tubular element and is supported by the stirring member, such that it can rotate about at least one axis of rotation incident on the longitudinal axis of the tubular body and such that it can be cyclically translated in at least one or more predetermined directions.

Preferably, the movements are a rotation of the washing and separating container about an axis perpendicular to its longitudinal axis and an alternative translation cycle, occurring at the same time as the above rotation.

As clearly shown by the illustrated exemplary embodiments, in order to mimic the movements of the hand of the surgeon, both the rotation and translation are periodic movements, and particularly the rotation is an oscillation about the above mentioned axis, whereas the translation is a movement along a vertical axis which periodically reverses its direction.

This will provide a combined oscillation and tilt movement of the washing and separating container, i.e. a tilt movement that can be cyclically repeated about different axes, thanks to the translational movement of the washing and separating container. According to a preferred variant embodiment, the washing and separating container is connected at its inlet via a two-way connection, to a saline vessel and a liposuctioned material vessel respectively, whereas its outlet is connected via a two-way connection to a waste product vessel and a collection vessel respectively.

With this configuration, the washing and separating container may be connected to the remaining components required for the target product generation process, thereby forming a closed system.

This is a particularly advantageous feature, as the probability of product contamination exponentially increases when there is no closed system, as all the products involved in the process, i.e. the saline and/or the liposuctioned material, are exposed to deterioration due to contact with air.

In view of optimizing the creation of a closed system, according to an improvement of the device of the present invention, the two-way connections have self-closing valves.

As more clearly shown by the figures annexed hereto, the use of self-closing valves provides automatic communication or separation between the areas upstream or downstream from the valve, in which the loading and collection devices (typically syringes with screw connectors) are connected, and the washing and separating container, by a simply connecting action.

Thus, as more clearly shown by the images, the operation of the self-closing valves allows introduction of material into the washing and separating container from the inlet port and removal thereof from the outlet port.

For further automation of the target product generation process, the washing and separating container is connected to the saline vessel via pumping means for controlling the washing flow.

In a possible embodiment, which is designed to standardize the process and optimize the formation of a closed system, the washing and separating container is connected to the waste fluid collection vessel through a solenoid-operated pinch valve.

The solenoid-operated pinch valve may be electronically controlled to open and close the connecting tube according to the process steps, and be synchronized and cooperate with the other actuators of the apparatus, with time intervals decided by the user or resulting from the processing operation of the process control unit.

As more clearly shown by the explanation of the method of the present invention, the pumping means advantageously operate in combination with the solenoid-operated pinch valve, such that the discharge passage is closed and the only available passage for the product formed in the process is the connector with the collecting syringe.

Preferably, the connector means of the fluid circuit are made of one piece with the washing and separating container.

The minimization of parts is known to be a key aspect in the design and construction of safety-critical systems: the use of coupling means formed of one piece with the container can provide a coupling and fixing system that is entirely integrated with the container and cannot be removed therefrom, without the implementation of removable parts that might affect the reliability of the connection and would pose cleaning and sanitization problems for the device and the apparatus of the present invention.

Furthermore, in a preferred variant embodiment, the device of the present invention comprises at least one electronic control unit, which electronic control unit has at least one input/output interface unit, at least one display unit, at least one processing unit containing processor means for executing a logic program.

This variant provides a device that can generate the target product for transplantation by an entirely automated process.

Finally, the invention allows the operation of the device of the present invention to be monitored.

Thus, in one embodiment of the invention, sensors are used to monitor process conditions and thus, directly or indirectly, successful processing of the material for transplantation.

These sensors may sense, for instance, process variables, such as pressure, temperature and movement of the stirring means, or may be physico-chemical sensors which sense, for instance, solute concentrations in the various parts of the system.

Sensor data may be later used for process optimization, as they can be useful for the setup of the electronic unit that regulates the operation of the device of the present invention, to obtain a standardized product.

As a result, the use of sensors, in combination with the features of the device of the present invention as described above can not only optimize automated operation of the device, but also have an information purpose, i.e. provide assessments of any kind, e.g. statistical or clinical assessments or else, about the generation of the target product.

Furthermore, sensor information can be processed by the device in real time while the process is being carried out, such that the operation may be set up and changed at each instant, for optimized product generation.

The present invention also relates to a device for preparing adipose tissue for transplantation from lobular fat extracted, for instance, by liposuction, said fat consisting of a solid component composed of adipocytes arranged in cell agglomerates of heterogeneous sizes, a fluid component comprising an oily component derived from lysis of adipocytes, blood residues and other liquid components, such as medicated saline solutions containing anesthetics, as used during the liposuction procedure.

Such device is composed of a washing and separating container with a washing chamber for washing the liposuctioned material, which container has at least one inlet and at least one outlet for the liposuctioned material to enter the washing chamber through the inlet and for at least part of said material, particularly the fluid component, to exit said chamber through the outlet.

The washing and separating container further has coupling members made of one piece therewith, for coupling the container to at least one support structure.

Advantageously, the washing and separating container is connected at said inlet via a two-way connection, to a saline vessel and a liposuctioned material vessel respectively, said outlet being connected via a two-way connection to a waste product vessel and a collection vessel respectively, and said two-way connections being equipped with self-closing valves.

In a possible embodiment, the washing and separating container is composed of a cylindrical body having two corresponding closing heads at its end sides, which closing heads are fixed at said at least one inlet and said at least one outlet, the two-way connections being formed of one piece with said closing heads.

The closing heads may be fixed to the container in any manner known in the art, but are preferably welded thereto before installation, for improved safety of the interior of the device.

It will be further appreciated that the present invention also relates to a method of preparing adipose tissue for transplantation, from lobular fat extracted, for instance, by liposuction, the fat consisting of a fluid component composed of an oily component, a blood component and/or sterile solutions and a solid component composed of cell fragments, cells and one or more cell macroagglomerates of heterogeneous size.

Particularly, the method of the present invention includes the steps of:

a) flushing a washing and separating container having a chamber for washing the liposuctioned material, an inlet and an outlet, by introducing a saline into said washing chamber through said inlet, b) introducing the liposuctioned material into the washing chamber through the inlet, c) stirring the washing and separating container to facilitate emulsion of fluid components, particularly the oily component with the sterile fluid substances, by the provision of emulsifying means, d) placing the washing and separating container in such a position as to obtain a stratification of the solid components on the liquid emulsion which constitute the fat contained in the washing chamber, particularly to obtain a solid component composed of cell fragments, cells and one or more cell agglomerates floating on an emulsion of the fluid components in the lower portion of the washing chamber in contact with the outlet of the washing and separating container, e) injecting a saline through the inlet and discharging the emulsion of fluid components from the washing chamber through the outlet of the washing and separating container, with density gradient removal of the emulsion of fluid components, These method steps are known and clearly disclosed by the above mentioned Patent Application WO2011/145075.

However, in the present Patent Application, at least step c) is carried out in automated fashion, the washing and separating container being coupled to stirring means via coupling means for releasably coupling said washing and separating container to said stirring means, drive means being provided for driving the stirring means.

As mentioned above concerning the device of the present invention, also the method advantageously affords repeatability, i.e. standardization of the washing and separating container stirring process, for accurate generation of an invariable product, always having the same chemical and physical properties.

Considering the characteristics of the device, in addition to step c), also steps a), d) and e) may be automated.

Furthermore, in a variant embodiment, an additional flushing step is provided, by introduction of a saline into the washing chamber through the inlet, at the same time as step b).

This arrangement ensures constant cleanness of the washing and separating container, and particularly its parts, such as the nets as described in WO2011/145075.

The above described solution is only allowed by the provision of the self-closing valves within the above described two-way connections.

Advantageously, step c) is obtained by a combination of a rotation or oscillation about an axis of rotation perpendicular to the longitudinal axis of the washing and separating container and a translation in at least one predetermined direction.

According to an improvement of this feature, stirring of the washing and separating container is carried out according to certain rotation and/or translation identification parameters.

This will advantageously allow this method step to be diversified according to the operating conditions and/or according to the product being processed or desired.

The identification parameters may be of any kind such as rotation/translation speed, angles, etc.

Also, a step may be provided in which said identification parameters are entered.

Alternatively, these parameters may be automatically calculated from the user settings of the above mentioned logic program, that will be clearly described by the figures annexed to the present Patent Application.

Furthermore, in a variant embodiment, a step is provided in which controls for operation of steps a) to e) are entered.

According to a further variant embodiment, the filling step a) is followed by a sub-step a1) in which said washing and separating container is stirred.

Since filling is used for removing air from within said washing and separating container, stirring of the latter during washing can optimize removal of air bubbles that are formed on the inner walls of the container.

Finally, it shall be noted that a particular advantageous aspect of the method of the present invention is the combination thereof with the use of sensors as described above.

These sensors can provide information about the development of each step, thereby allowing the user to thoroughly monitor each step.

For example, the individual steps may be divided into reversible sub-steps, each distinguished and differentiated from the others by critical parameters such as pressure, temperature, orientation, amplitude, frequency and duration of movements, etc.

The use of sensors will provide manual or automatic monitoring, e.g. according to a predetermined algorithm that can process the information received at each instant from the sensors.

These and other features and advantages of the present invention will appear more clearly from the following description of a few embodiments, illustrated in the annexed drawings, in which:

FIGS. 2a to 2d show details of the device of the present invention;

FIGS. 3a to 3d show the steps of the method of the present invention;

It should be understood that the figures annexed hereto only concern a possible embodiment of the device and method of the present invention and shall be intended without limitation, as having the purpose of merely explaining the inventive principle of the present invention, i.e. the provision of a device and a method that can standardize the process for preparing adipose tissue for transplantation from lobular fat.

Figure 1A:
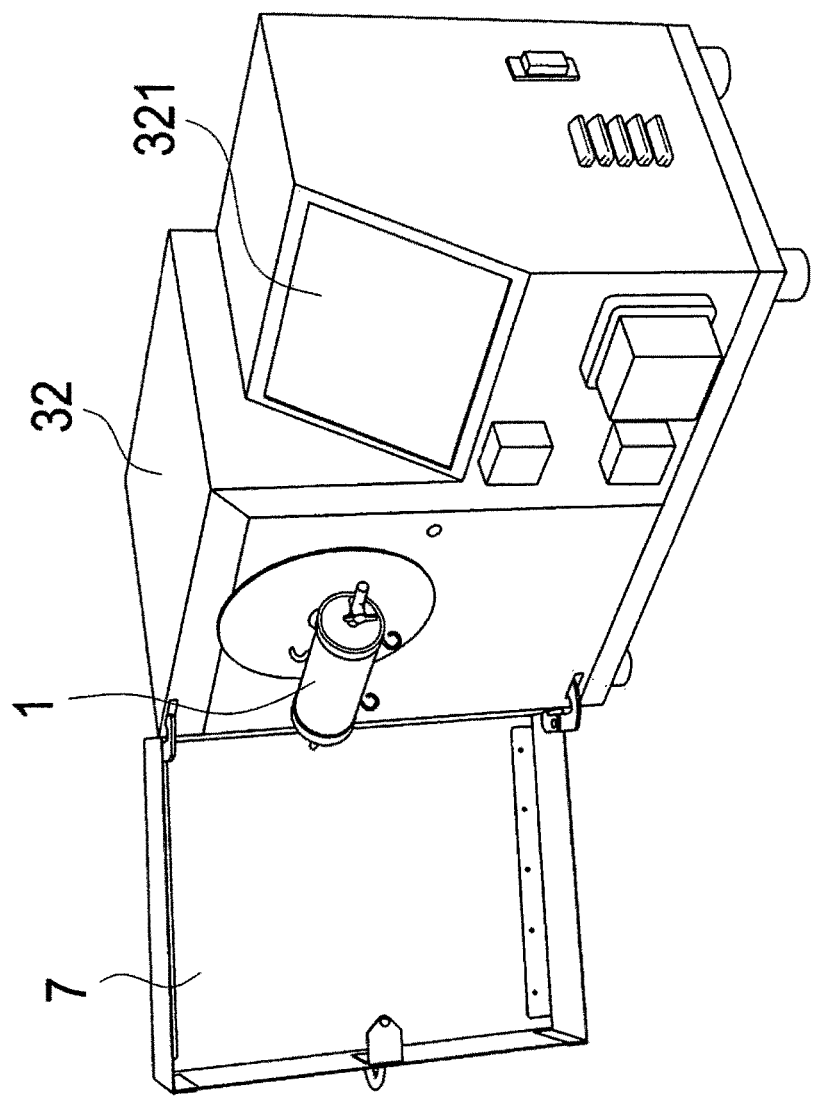
FIGS. 1a and 1b show two perspective views of the device of the present invention.
Figure 1B:
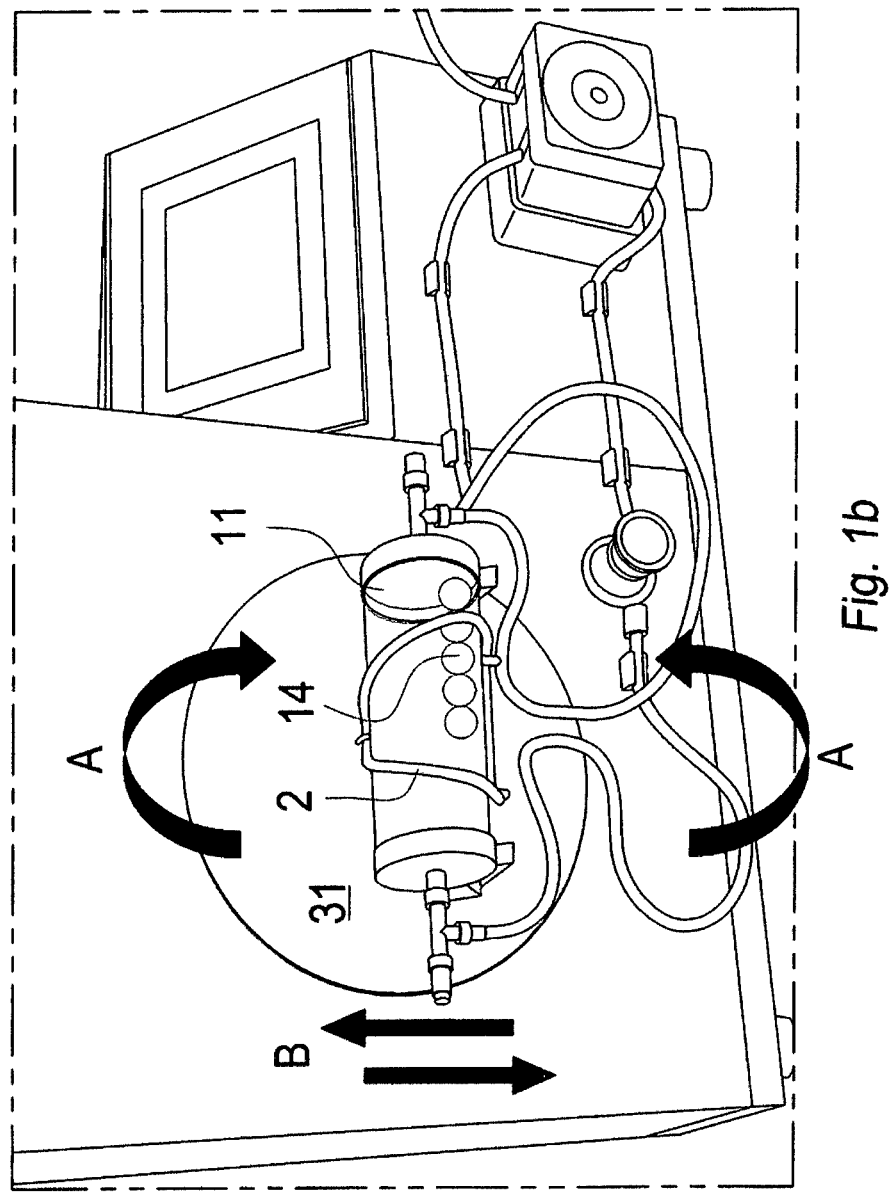

Particularly referring to the figures, FIGS. 1a and 1b show a device for preparing adipose tissue for transplantation from a solid component composed of adipocytes arranged in cell agglomerates of heterogeneous sizes, a fluid component comprising an oily component derived from lysis of adipocytes, blood residues and other liquid components, such as medicated saline solutions containing anesthetics, as used during the liposuction procedure.

The device comprises at least one washing and separating container 1 having a washing chamber 11 for washing the liposuctioned material, which washing and separating container 1 has at least one inlet 12 and at least one outlet 13 for the liposuctioned material to enter the washing chamber 11 through the inlet 12 and for at least part of said material, particularly the fluid component, to exit said chamber 11 through the outlet 13.

The washing and separating container 1 is coupled to stirring means via coupling means 2 for releasably coupling the washing and separating container 1 to the stirring means.

Drive means are also provided, for driving the stirring means, such stirring means comprising a stirring member 31 supported by a support structure 32.

The washing and separating container 1 is releasably coupled to the stirring member 31 via the coupling means 2, and the stirring member 31 is driven by said drive means.

Emulsion generating means 14 are also provided in the washing chamber 11, for generating an emulsion of the fluid components by mechanical stirring.

It shall be noted that the washing and separating container may comprise all the features as disclosed in the International Patent Application WO2011/145075.

FIGS. 1 and 1b do not show the coupling between the stirring member 31 and the drive means that drive it, but such coupling may be provided with any known method that can ensure transmission between a motion generating member, one or more mechanisms that perform the required movements, and the functional actuator members.

The coupling means 2 for coupling the container to the stirring member 31 may consist of any element that can rigidly join the container 1 to the stirring member 31.

Figure 2B:
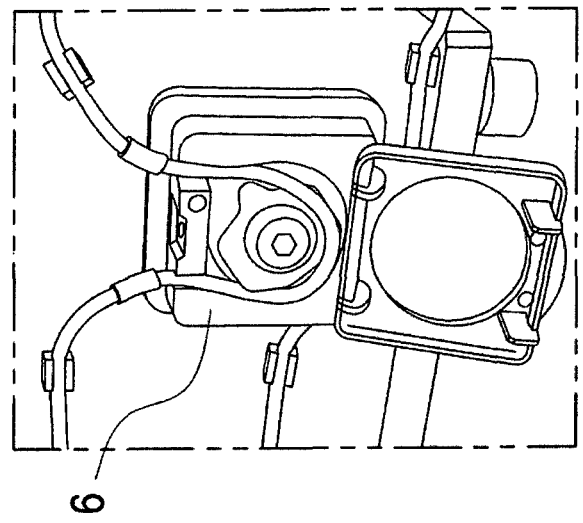
Figure 2A:
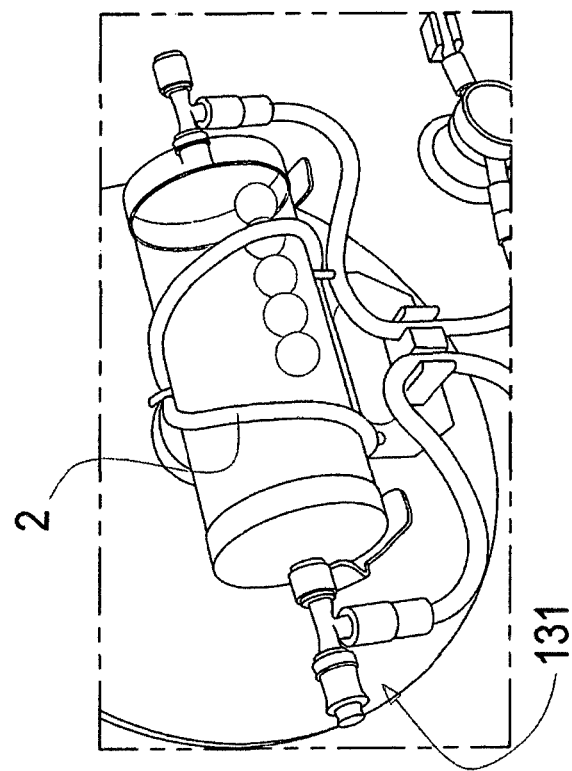

In the particular case of FIGS. 1b and 2a, the coupling means 2 consist of an elastic element 2 that is rigidly joined to the stirring member 31 and surrounds the outer surface of the container 1.

Other clamp or jaw elements may be also used.

Figure 5:
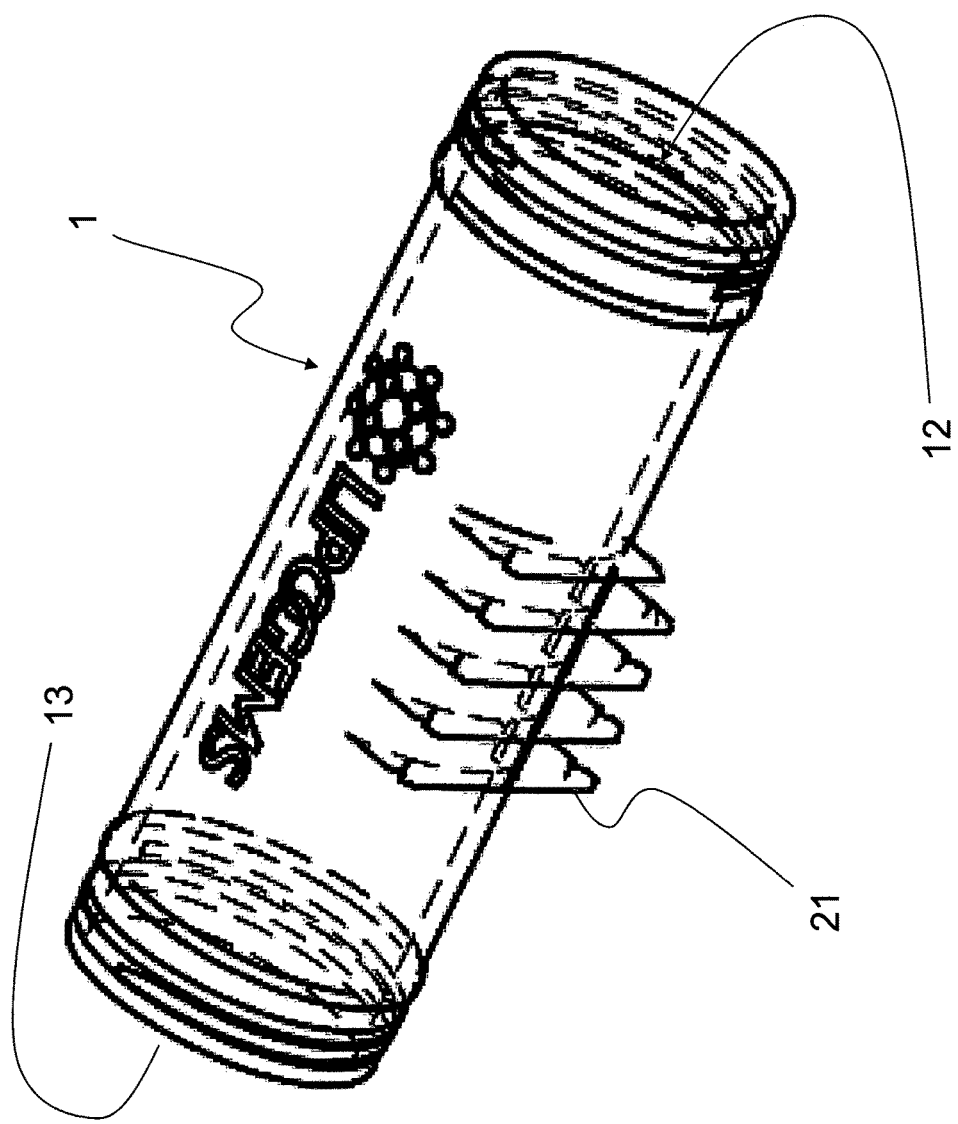
FIG. 5 shows a possible embodiment of the washing and separating container provided in the device of the present invention.

In a possible embodiment as shown in FIG. 5, the washing and separating container 1 has coupling means formed of one piece with the walls of the tubular body of the container 1.

These coupling means consist of members 21 that cooperate with a corresponding engagement seat integrally formed on the stirring member 31.

Particularly the members 21 may engage with the stirring member 31 by means of a sliding or bayonet connector equipped with a lock device.

This will avoid the need of forming the coupling means as shown in FIG. 2a.

As shown in the figures, the container 1 consists of a tubular element.

The stirring member 31 supports the washing and separating container 1 such that it can rotate or oscillate about an axis of rotation incident on the longitudinal axis of the washing and separating container 1 and such that it can be translated in at least one predetermined direction.

Arrows A and B of FIG. 1b show the possible movements of the stirring member 31, and hence the container 1.

The rotation and translation occur simultaneously and periodically, i.e. the drive means move the stirring member 31 such that the container periodically moves up and down, as shown by arrow B, while periodically rotating to the right and left, as shown by arrow A.

This will not simply provide a mechanical transmission system, but a system in which constraints are not fixed, but set by user controls, as more clearly explained below.

Figure 3A:
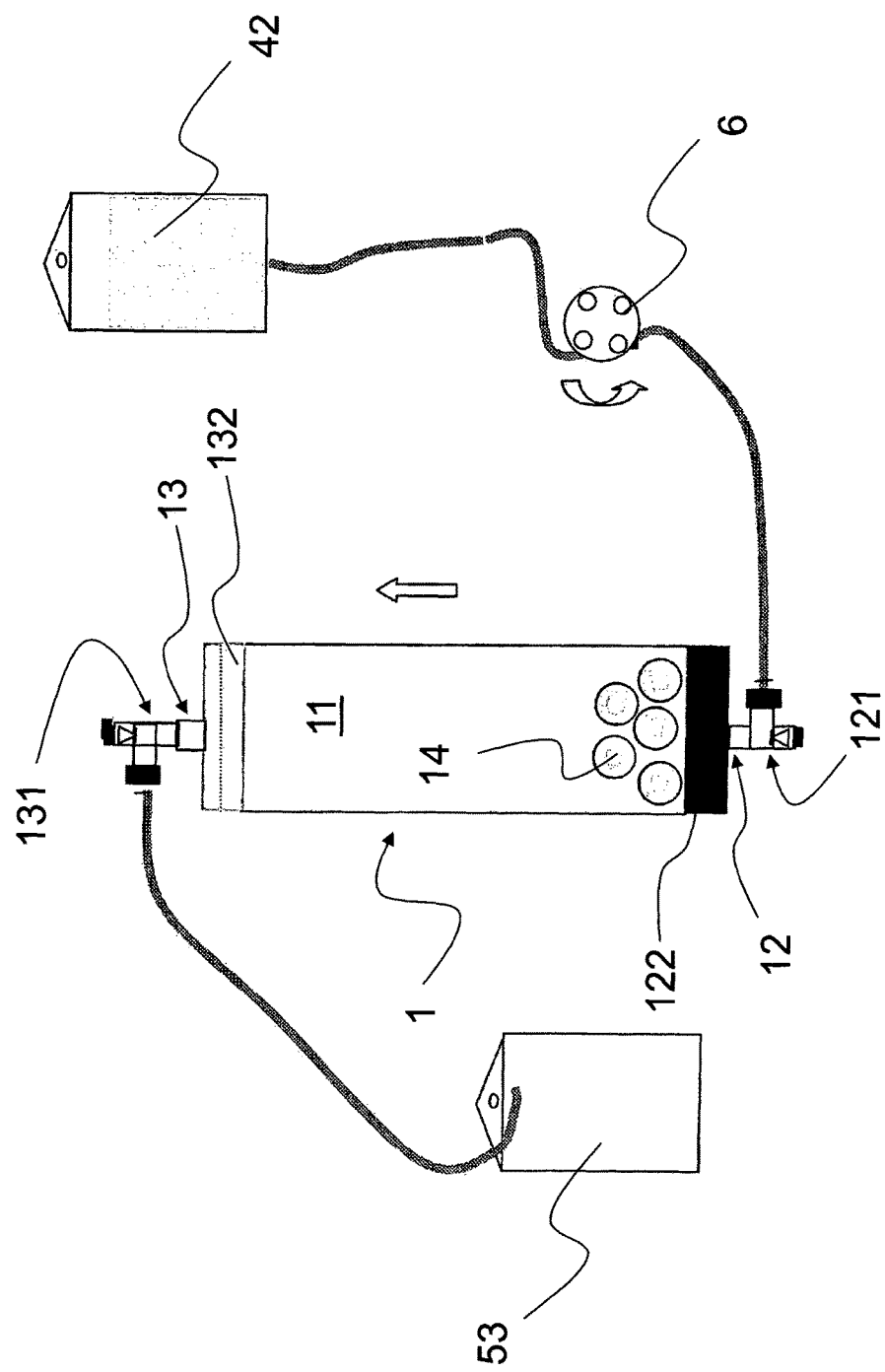

FIGS. 3a and 3b show a possible configuration of the washing and separating container 1, in which the container 1 is connected at the inlet 12, via a two-way connection 121, to a saline vessel 42 and a liposuctioned material vessel 52 respectively.

The outlet 13 is connected via a two-way connection 131 to a waste product vessel 53 and a collection vessel 54 respectively.

Preferably the connections 121 and 131 are equipped with self-closing valves.

Particularly the cylindrical body of the container 1 has the inlet 12 and the outlet 13 consisting of two closing heads 122 and 132 which may be formed of one piece with the two-way connections 121 and 131.

Each two-way connection has at least one self-closing valve.

As explained below, for example, when the syringe 52 is connected to the valve 121, see FIG. 3b, the self-closing valve allows the liposuctioned material to be introduced into the container 1, but as soon as the syringe is disconnected, the self-closing valve closes to prevent exit of the material and to isolate the inner environment.

As clearly shown in FIGS. 3a to 3d, the system composed of the container 1 and the various parts connected thereto is a closed system, with the connecting tubes integrated in said system, which may be mounted to the structure 32 of FIGS. 1a and 1b.

Both the closing heads 122, 132 of the container 1 and the connections 121 and 131 with their self-closing valves may be connected by screw, interlocking, welding or chemical bonding arrangements, or by complex connections, as needed, provided that they can withstand with appropriate safety margins the mechanical and pressure stresses exerted thereon during treatment and extraction of the material being processed.

The two-way connections 121 and 131 allow two different inlet or outlet ports to be integrated into a single connection.

Figure 6A:
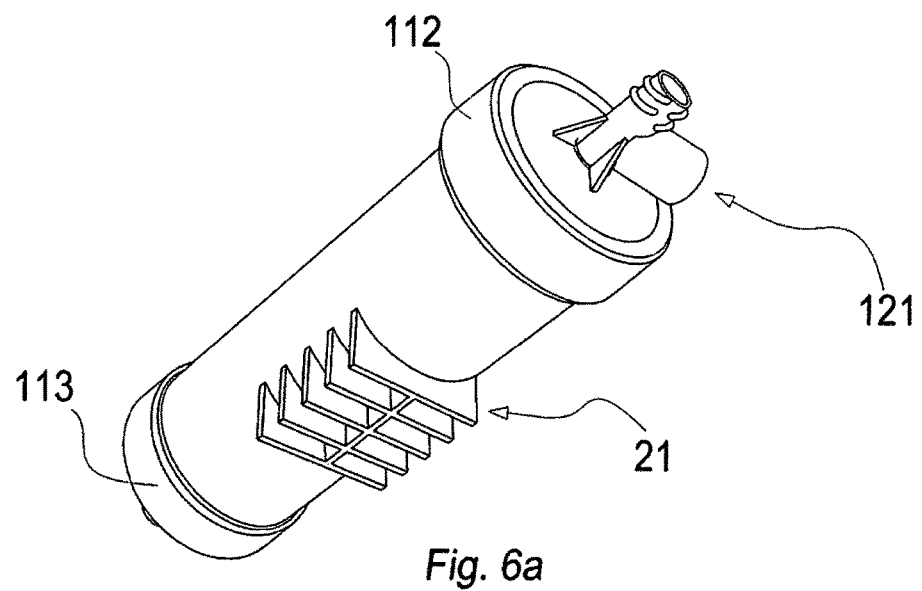
FIGS. 6a and 6b show two views of the washing and separating container according to a possible embodiment.
Figure 6B:
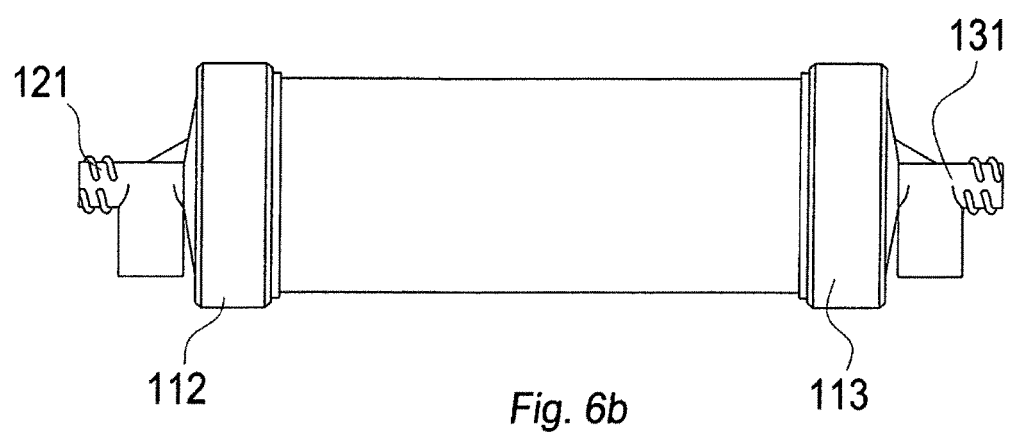

FIGS. 6a and 6b show a possible embodiment of the two-way connections.

Particularly, the washing and separating container qq is composed of a cylindrical body having two corresponding closing heads 112 and 113 at its end sides, such heads being fixed at the inlet 12 and at the outlet 13.

Preferably, the closing heads 112 and 113 are formed integrally, i.e. of one piece, with the two-way connections 121 and 131.

Furthermore, the washing and separating container 1 is connected to the saline container 42 through pumping means 6, e.g. a peristaltic pump or the like.

In a possible embodiment, the device of the present invention may include a safety door 7, which causes the process to stop as soon as it is opened.

FIGS. 2a to 2d further show the particular arrangements that can be envisaged both for the connecting tubes and for the pumping means 6 attached to the support structure 32.

Particularly, FIG. 2c shows a possible component of the system, i.e. a solenoid-operated pinch valve 8 which connects the washing and separating container 1 to the collection vessel 53 of FIG. 3b, in which the solenoid-operated pinch valve 8 is schematically represented by knot that closes the tube 81.

Thus, the solenoid-operated pinch valve 8, which is preferably controlled by the electronic unit, allows the tube 81 to automatically closed and opened in synchronism with the process, and when the tube 81 is required to be closed, the solenoid-operated valve closes and the area defined by the container 1 is isolated from the discharge bag 53.

Particularly referring to FIGS. 1a and 1b, the device of the present invention includes at least one electronic control unit, which electronic control unit has at least one input/output interface unit, at least one display unit, at least one processing unit containing processor means for executing a logic program.

The electronic control unit is contained in the support structure 32 and the display unit and the input/output interface unit are preferably integrated in a screen 321, such as a touchscreen or the like.

The input/output interface 321 may be used to enter the controls to set the operation of the logic program.

Then, the logic program generates controls to regulate the movements of the stirring member 31 and carry out the method of the present invention, as initially shown in FIGS. 3a to 3d.

The method of the present invention is a method of preparing adipose tissue for transplantation, from lobular fat extracted, for instance, by liposuction, the fat consisting of a fluid component composed of an oily component, a blood component and/or sterile solutions and a solid component composed of cell fragments, cells and one or more cell macroagglomerates of heterogeneous size.

The method of the present invention includes the steps of:

a) filling the washing and separating container 1, as shown in FIG. 3a.

The pumping means 6 pump the saline contained in the vessel 42 into the washing chamber 11.

The saline fills the entire washing chamber 11, thereby completely removing air through the inlet 12 and the two-way connection 121.

b) introducing the liposuctioned material into the washing chamber 11, as shown in FIG. 3b.

A syringe 52 is introduced into one of the two ports of the two-way connection 121 and the liposuctioned material is pushed into the washing chamber 11 through the inlet 12.

Any amount of liposuctioned material may be injected using a plurality of syringes.

Figure 3C:
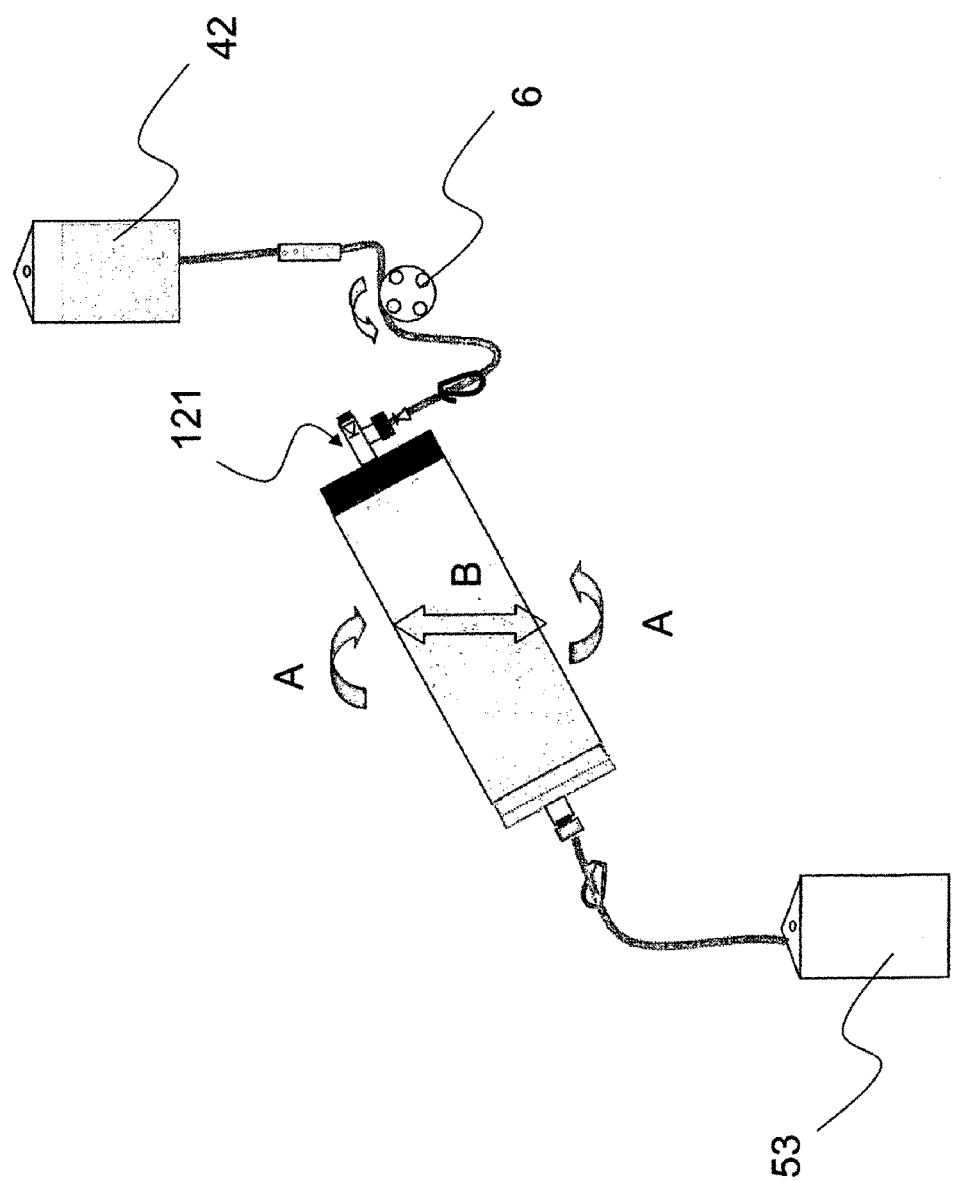
Figure 3D:
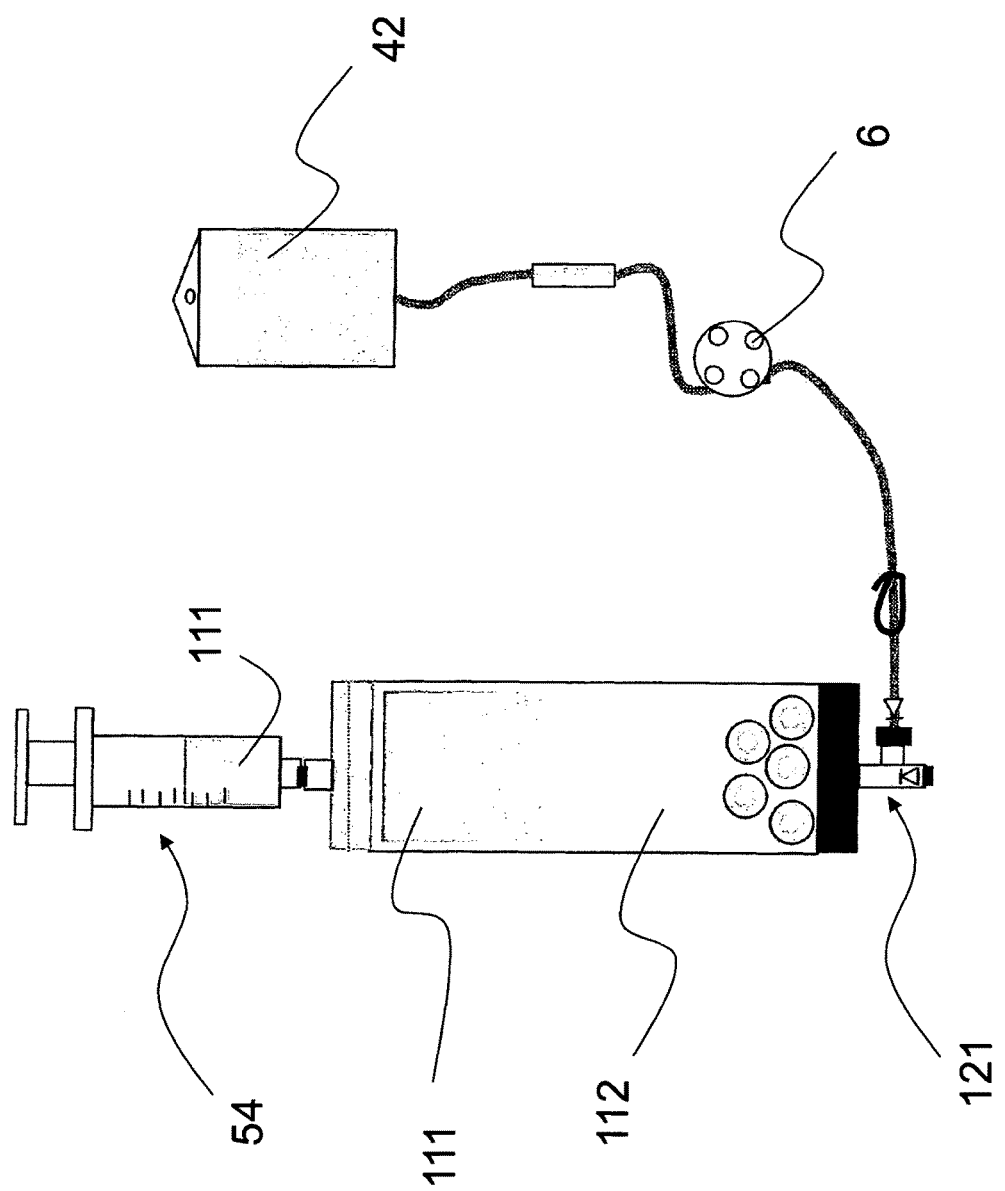

The provision of a solenoid-operated pinch valve 8 allow regulation of the waste fluid that flows from the outlet 13 and is collected in the vessel 53.

c) stirring the washing and separating container 1, as shown in FIG. 3c, to facilitate emulsion of fluid components, particularly the oily component with the sterile fluid substances, by the provision of emulsifying means 14 for generating an emulsion of the fluid components.

d) placing the washing and separating container 1, as shown in FIG. 3d, in such a position as to obtain a stratification of the solid components 111 on the liquid emulsion 112.

Particularly, the container 1 is in such a position that the container 1 has its longitudinal axis parallel to a vertical axis, whereby from FIG. 3a to FIG. 3D the container 1 is rotated by 180°.

Thus, the material in the washing chamber 11 has a solid component 111 composed of cell fragments, cells and one or more cell agglomerates floating on an emulsion of the fluid components 112 in the lower portion of the washing chamber 11 in contact with the outlet 13 of the washing and separating container 1.

e) injecting saline and withdrawing the solid component 111 for use in the transplantation.

The syringe 54 is connected to the two-way connection 131 associated with the outlet 13 of the container 1.

The pumping means 6 pump the saline from the vessel 42 into the washing chamber 11 through the inlet 12.

Pressure in the washing chamber 11 increases until the processed material is ejected from the outlet connected to the collecting syringe.

Step c) is carried out in automated fashion, the washing and separating container 1 being coupled to stirring means, as described above.

As better explained below, steps a), c), d) and e) are preferably also automated.

In step b), as shown in FIG. 3*b*, the saline may be simultaneously introduced into the container 1 from the vessel 42.

As shown in FIG. 3*c*, step c), in which the container 1 is stirred, is obtained by a combination of a rotation or oscillation, as shown by arrow A, about an axis of rotation perpendicular to the longitudinal axis of the washing and separating container 1 and a translation, as shown by arrow B, in at least one predetermined direction.

Preferably, the oscillation has an amplitude of about 70 mm and a frequency not exceeding 6.5 Hz.

Advantageously, step a) is followed by a sub-step a1) in which the washing and separating container 1 is stirred.

In a possible embodiment, stirring of said washing and separating container 1 is carried out according to certain rotation and/or translation identification parameters.

These identification parameters may be selected and set by a user.

A user may also select and set a sequence of variation of such parameters, e.g. frequency and amplitude of oscillation and tilt, orientation of movement axes, time-dependent washing flow, from predetermined sequences, treatment programs and profiles, or according to physical and chemical detections by sensors that may be provided on the apparatus.

Particularly, the identification parameters or the sequences or logics of variation of such parameters during treatment, may be entered through the logic program executed by the above described processing unit.

Likewise, like the identification parameters, operating controls for carrying out said steps from a) to e) may be entered.

FIGS. 4*a* to 4*h* show different screens of the user interface as displayed by the touchscreen 321.

Figure 4A:
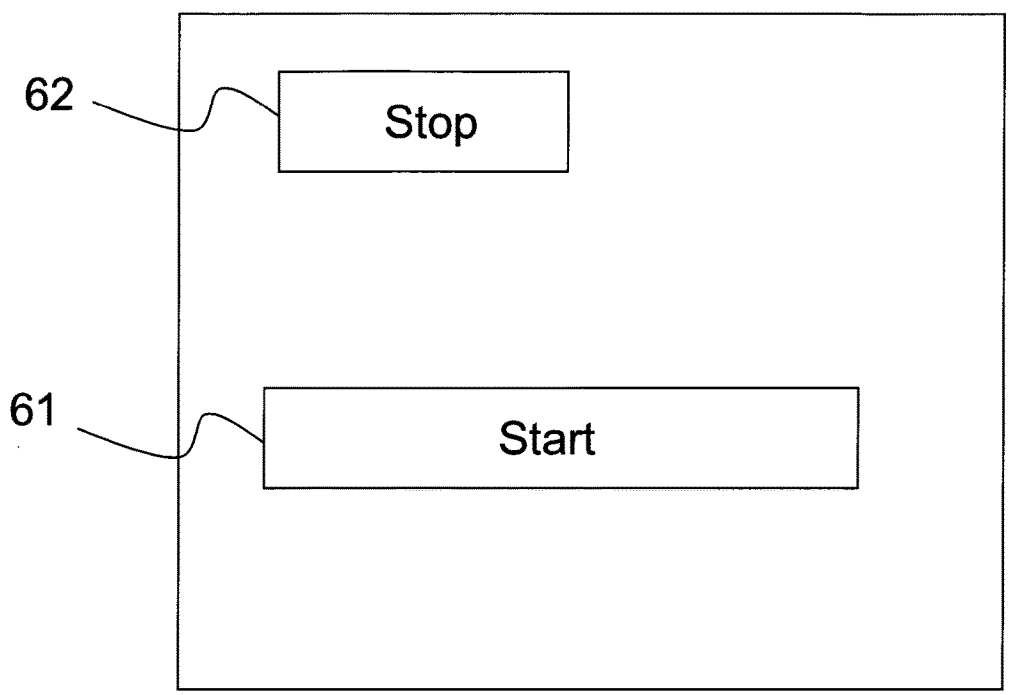
FIGS. 4a to 4h show different screens of the user interface as displayed by the device of the present invention.

Once the container 1 is mounted to the stirring member 31, the program is started and a start screen is displayed, as shown in FIG. 4*a*, whereby the user may start the treatment by pressing the start button 61.

Each screen may have a button 62 for stopping the process.

Figure 4B:
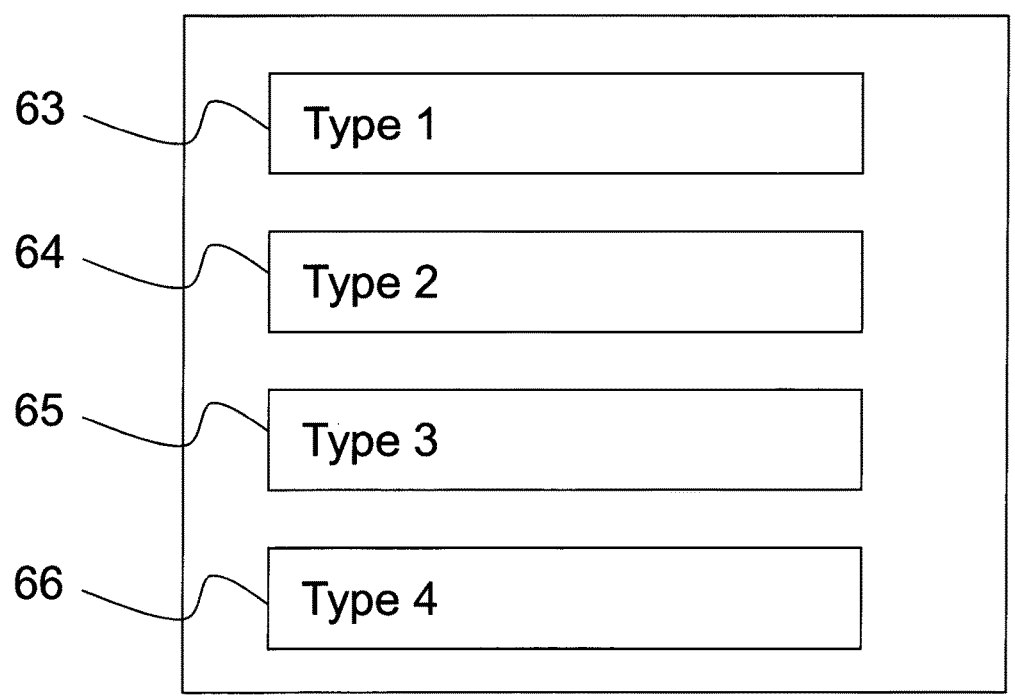
Figure 4C:
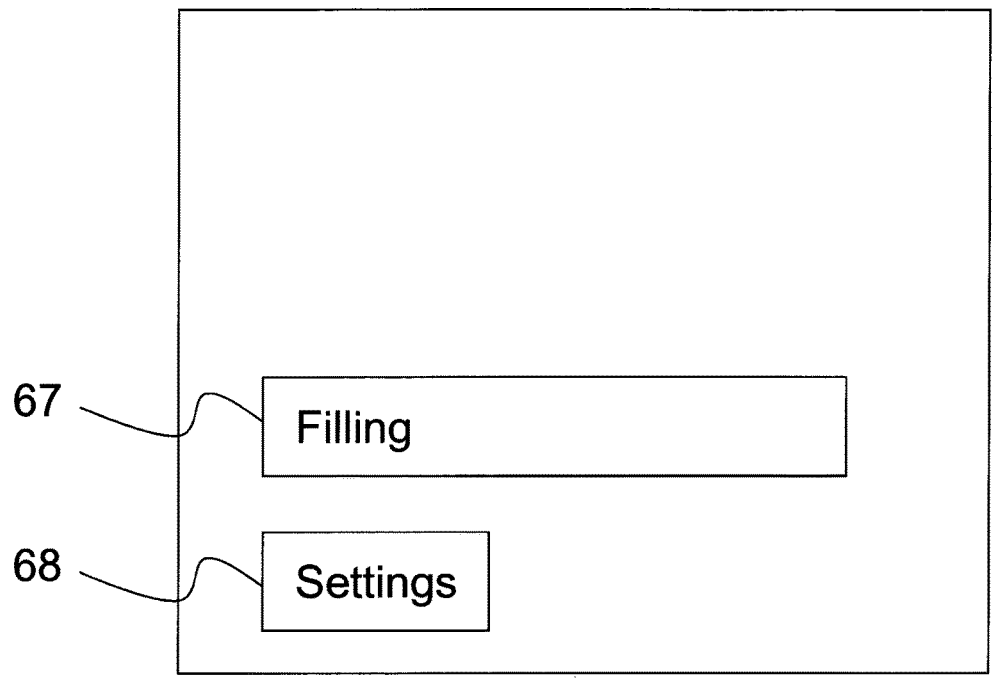

As soon as the process starts, the user may select the type of final product to be obtained, as shown in FIG. 4*b*: the user selects one of the buttons 63, 64, 65, 66 to chose a product type, having differentiated chemical and physical properties.

The program provides a series of preset types, although the characteristics of the product may be set manually.

Obviously, each type will be associated with different identification parameters.

According to the selected type, the program may set, for example, the amount of liposuctioned material and the flow of saline to be introduced into the washing chamber 11, the washing time, the speed, orientation, frequency and amplitude of the movements and the duration thereof.

The products may be also differentiated according to the type of container 1 to be used in the process, both in terms of size and parts thereof, e.g. the nets used therein, as described in greater detail in WO2011/145075.

The inlet and outlet 12 and 13 are connected to the vessels as described above and the button 67 is selected to start the pumping means 6 and fill the container with saline.

Thus, the filling step starts, and the container 1 is placed with its longitudinal axis in a vertical position, with the inlet 12 at a lower position than the outlet 13.

Each screen may include a button 68 for the user to change the process settings.

Furthermore, one or more monitoring screens may be provided, for checking whether the container 1 is properly connected.

Figure 4D:
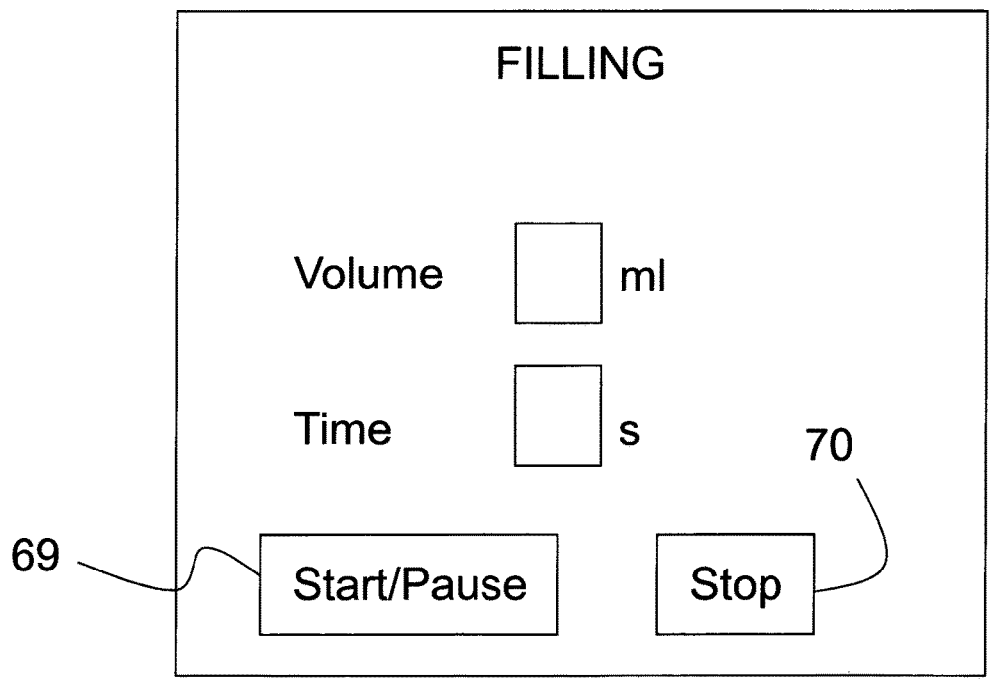

Then the filling step starts, as shown in FIG. 4*d*, and the program displays a screen that shows the amount and volume of saline that is being introduced, and allows the process may be paused, by button 69 or stopped, by button 70.

The filling step may automatically stop as soon as the preset volume is reached.

Figure 4E:
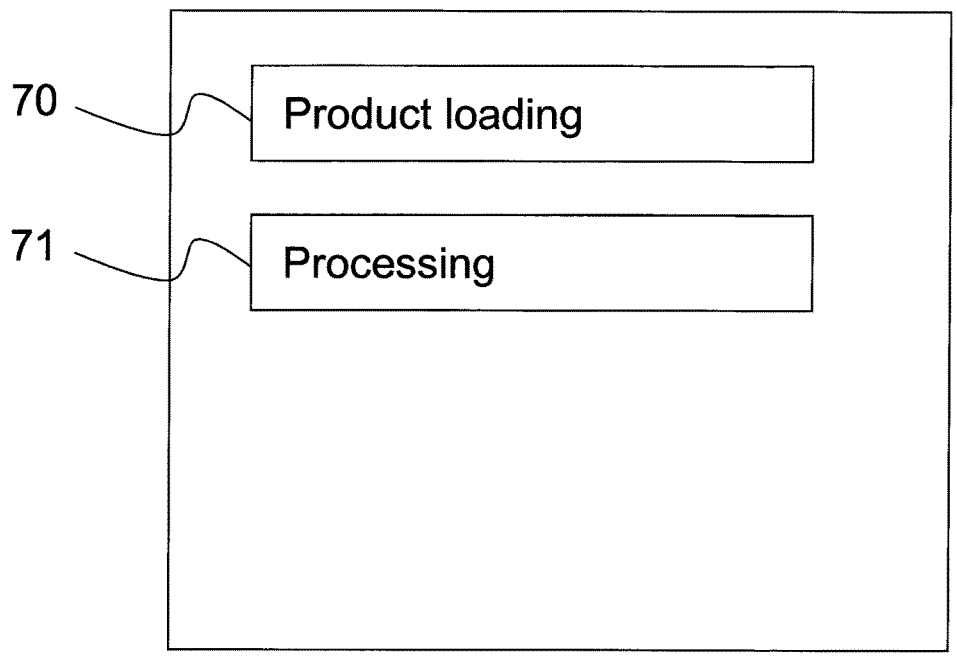

FIG. 4*e* shows the next screen, through which loading of the liposuctioned material or processing may be started, by buttons 70 or 71 respectively.

Figure 4F:
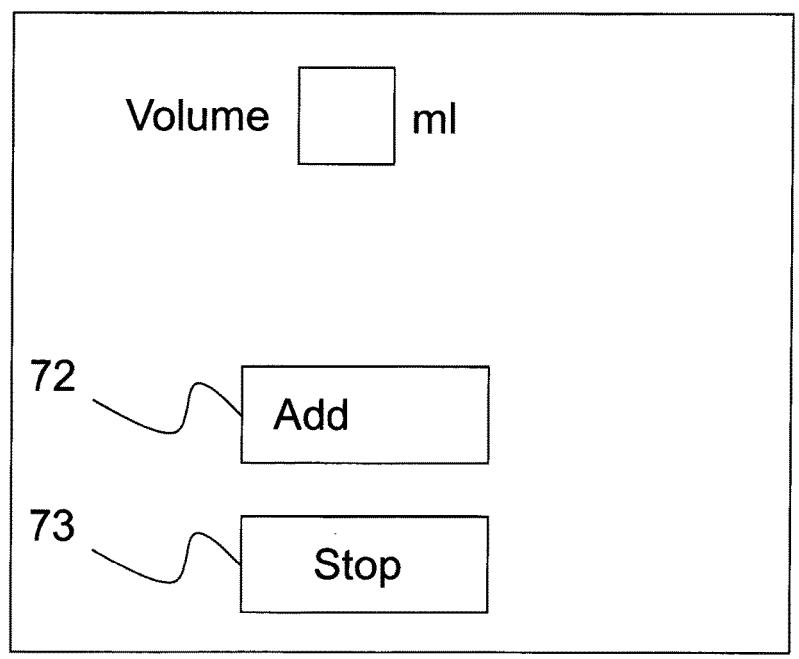

The user starts loading the liposuctioned material, and the screen of FIG. 4*f* shows the loaded amount and more lipoisuctioned material may be added, by button 72, or loading may be stopped, by button 73.

Figure 4G:
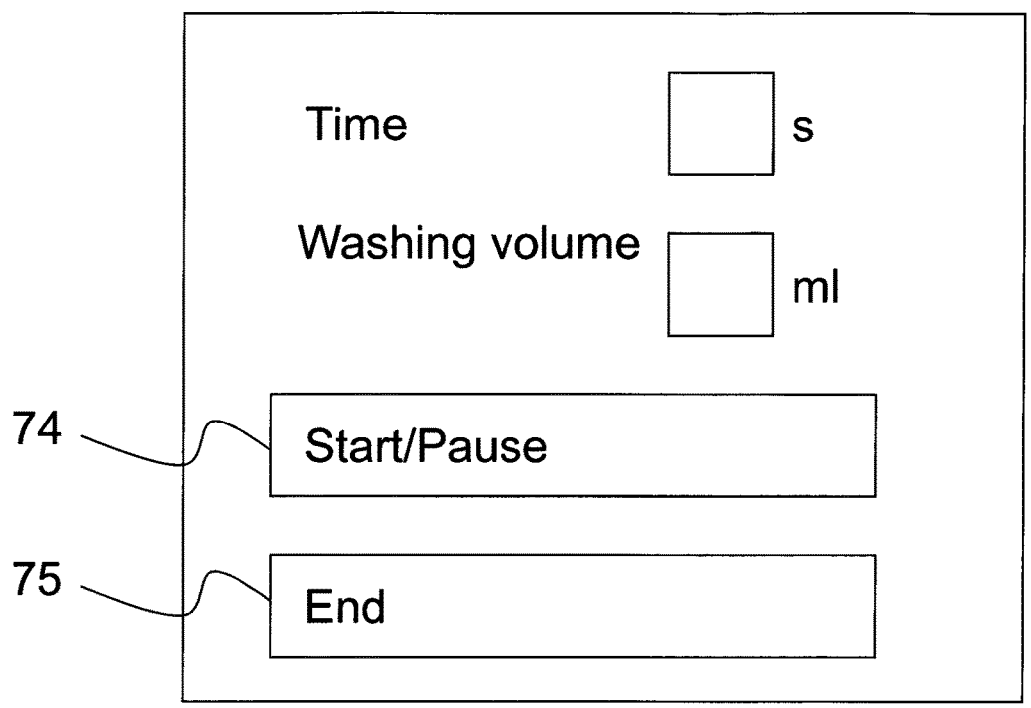
Figure 4H:
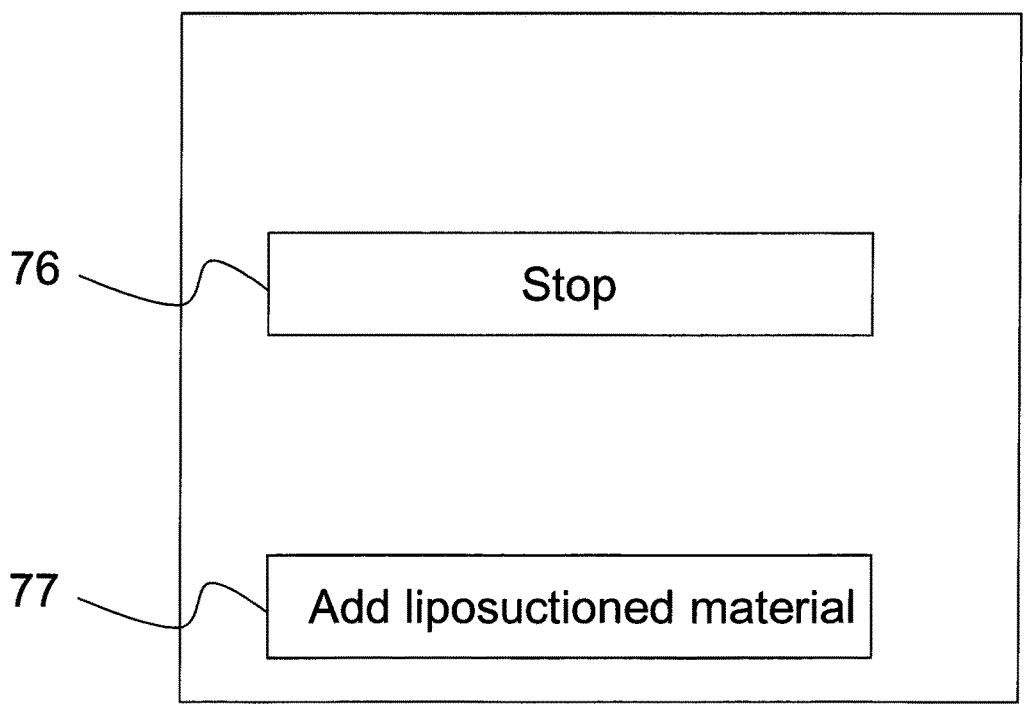

When pressing the button 73, the program displays the screen of FIG. 4*g* through which stirring of the container 1 may be started/paused by button 74 or stopped, by button 75.

Furthermore, the overall stirring time and the washing volume may be monitored.

Once the stirring process has ended, the screen 4*h* will be displayed, through which the process may be terminated, by button 76, or new liposuctioned material may be loaded, by button 77, to repeat the stirring step.

When the button 76 is selected, the program will prompt for the insertion of a syringe to collect the product so formed in the washing chamber, as described with respect to FIG. 3*d*.

Now the user may decide whether to repeat the process to increase the amount of generated product, or end the process if an adequate amount of product has been obtained thereby.

The invention claimed is:

1. A device for preparing adipose tissue for transplantation from lobular fat material extracted by liposuction, said fat material comprising (a) a solid component composed of adipocytes arranged in cell agglomerates of heterogeneous sizes, and (b) a fluid component comprising one or more of an oily component derived from lysis of adipocytes, blood residues, and medicated saline solutions containing anesthetics, as used during the liposuction procedure, said device comprising at least one washing and separating container (1) having a washing chamber (11) for washing the liposuctioned material, said washing and separating container (1) having at least one inlet (12) and at least one outlet (13) for the liposuctioned material to enter the washing chamber (11) through the inlet (12) and for at least part of said material, separated from the fluid component, to exit said chamber (11) through the outlet (13), wherein said washing and separating container (1) is coupled to stirring means via coupling means (2) for releasably coupling said washing and separating container (1) to said stirring means, said stirring means provides drive means for driving said stirring means, said stirring means comprises a stirring member (31) supported by a support structure (32), said washing and separating container (1) being releasably coupled to said stirring member (31) via said coupling means, and said stirring member (31) being driven by said drive means, said washing chamber (11) provides emulsion generating means (14) for generating an emulsion of the fluid components by mechanical stirring, and said washing and separating container (1) comprises a tubular element, the stirring member (31) supporting said washing and separating container (1) such that it can rotate about at least one axis of rotation incident on the longitudinal axis of the washing and separating container and such that it can be cyclically translated in at least one or more predetermined directions.

2. A device as claimed in claim 1, wherein
said washing and separating container (1) is connected at said inlet (12), via a two-way connection (121), to a saline vessel (42) and a liposuctioned material vessel (52) respectively, and
said outlet (13) is connected, via a two-way connection (131), to a waste product vessel (53) and a collection vessel (54), respectively.

3. A device as claimed in claim 2, wherein said two-way connections (121, 131) have self-closing valves.

4. A device as claimed in claim 2, wherein said washing and separating container (1) is connected to said saline container (42) through pumping means (6).

5. A device as claimed in claim 2, wherein said washing and separating container (1) is connected to said collection vessel (54) through a solenoid-operated pinch valve (55).

6. A device as claimed in claim 1, wherein said coupling means (2) are made of one piece with said washing and separating container (1).

7. A device as claimed in claim 1, further comprising at least one electronic control unit, said electronic control unit having at least one input/output interface unit (321), at least one display unit (321), and at least one processing unit containing processor means for executing a logic program.

8. A device as claimed in claim 1, further comprising at least one sensor for detecting identification parameters concerning the movement of said washing and separating container and/or concerning the solution contained in said container.

9. A device as claimed in claim 1, wherein the stirring member (31) simultaneously rotates the washing and separating container (1) such that the container periodically moves to the left and right, and cyclically translates the washing and separating container (1) such that the container periodically moves up and down.

10. A device for preparing adipose tissue for transplantation from lobular fat material extracted by liposuction, said fat material comprising (a) a solid component composed of adipocytes arranged in cell agglomerates of heterogeneous sizes, and (b) a fluid component comprising one or more of an oily component derived from lysis of adipocytes, blood residues, and medicated saline solutions containing anesthetics, as used during the liposuction procedure,
said device comprising a washing and separating container (1) having a washing chamber (11) for washing the liposuctioned material, said washing and separating container (1) having at least one inlet (12) and at least one outlet (13) for the liposuctioned material to enter the washing chamber (11) through the inlet (12) and for at least part of said fluid component to exit said chamber (11) through the outlet (13),
wherein said washing and separating container (1) has coupling members (2) made of one piece with said container (1), for coupling said container (1) to at least one support structure.

11. A device as claimed in claim 10, wherein
said washing and separating container (1) is connected at said inlet (12), via a two-way connection (121), to a saline vessel (42) and a liposuctioned material vessel (52), respectively,
said outlet (13) is connected via a two-way connection (131) to a waste product vessel and a collection vessel (53), respectively, and
said two-way connections (121, 131) are complemented by self-closing valves.

12. A device as claimed in claim 10, wherein
said washing and separating container comprises a cylindrical body having two corresponding closing heads at its end sides, said closing heads being fixed at said at least one inlet and said at least one outlet, and
said two-way connections are made of one piece with said closing heads.

13. A method of preparing adipose tissue for transplantation, from lobular fat material extracted by liposuction, said fat material comprising (a) a fluid component comprising one or more of an oily component, a blood component, and/or sterile solutions, and (b) a solid component comprising cell fragments, cells, and one or more cell macroagglomerates of heterogeneous size,
said method comprising the steps of:
a) flushing a washing and separating container having a chamber for washing the liposuctioned material, an inlet and an outlet, by introducing a saline into said washing chamber through said inlet,
b) introducing the liposuctioned material into said washing chamber through said inlet,
c) stirring said washing and separating container to facilitate emulsion of the fluid components with the sterile fluid substances, by emulsifying means,
d) placing the washing and separating container in such a position as to obtain a stratification of the solid components on the liquid emulsion, which constitutes the fat contained in the washing chamber, to obtain a solid component composed of cell fragments, cells, and one or more cell agglomerates floating on an emulsion of the fluid components in the lower portion of the washing chamber and in contact with the outlet of the washing and separating container, and
e) injecting a saline through said inlet and discharging the emulsion of fluid components from the washing chamber through the outlet of the washing and separating container, with density gradient removal of the emulsion of fluid components,
wherein
at least step c) is carried out in automated fashion, said washing and separating container being coupled to stirring means via coupling means for releasably coupling said washing and separating container to said stirring means, and
said stirring means provides drive means for driving said stirring means.

14. A method as claimed in claim 13, wherein steps a), c), d) and e) are automated.

15. A method as claimed in claim 13, further comprising an additional flushing step by introducing a saline into said washing chamber through said inlet, at the same time as step b).

16. A method as claimed in claim 13, wherein step c) is obtained by a combination of a rotation or oscillation about an axis of rotation perpendicular to the longitudinal axis of said washing and separating container and a translation in at least one predetermined direction.

17. A method as claimed in claim 16, wherein stirring of said washing and separating container is carried out according to certain rotation and/or translation identification parameters.

18. A method as claimed in claim 17, further comprising a step in which said identification parameters are entered.

19. A method as claimed in claim 13, further comprising a step in which controls for operation of said steps a) to e) are entered.

20. A method as claimed in claim 13, wherein step a) is followed by a sub-step a1) in which said washing and separating container is stirred.

\* \* \* \* \*